(12) United States Patent
Gueller et al.

(10) Patent No.: US 10,987,666 B2
(45) Date of Patent: Apr. 27, 2021

(54) METERING APPARATUS

(71) Applicant: Chemspeed Technologies AG, Fullinsdorf (CH)

(72) Inventors: Rolf Gueller, Herznach (CH); Michael Schneider, Frick (CH); Thomas Thaler, Laufen (CH); Markus Schindler, Ennetburgen (CH)

(73) Assignee: Chemspeed Technologies AG, Fullinsdorf (CH)

( * ) Notice: Subject to any disclaimer, the term of this patent is extended or adjusted under 35 U.S.C. 154(b) by 35 days.

(21) Appl. No.: 15/525,462

(22) PCT Filed: Nov. 9, 2015

(86) PCT No.: PCT/CH2015/000165
§ 371 (c)(1),
(2) Date: May 9, 2017

(87) PCT Pub. No.: WO2016/074105
PCT Pub. Date: May 19, 2016

(65) Prior Publication Data
US 2017/0322068 A1     Nov. 9, 2017

(30) Foreign Application Priority Data

Nov. 10, 2014   (CH) ..................................... 1737/14

(51) Int. Cl.
*B01L 3/02*       (2006.01)
*G01G 17/06*     (2006.01)
(Continued)

(52) U.S. Cl.
CPC ............ *B01L 3/0227* (2013.01); *B65D 83/42* (2013.01); *G01G 13/2851* (2013.01);
(Continued)

(58) Field of Classification Search
CPC ............... G01N 35/10; G01N 35/0099; G01N 35/1072; G01N 2033/0091;
(Continued)

(56) References Cited

U.S. PATENT DOCUMENTS 4,023,716 A  *  5/1977  Shapiro ................. B01L 3/0279
                                                           222/309
4,586,546 A  *  5/1986  Mezei ................. G01N 35/1011
                                                              141/2
(Continued)

FOREIGN PATENT DOCUMENTS

CN         1575409 A        2/2005
CN       201215496 Y        4/2009
(Continued)

*Primary Examiner* — Andrew D StClair
(74) *Attorney, Agent, or Firm* — The Webb Law Firm

(57) ABSTRACT

A metering apparatus including a scale on which a metering head is disposed in such a manner that the scale measures the weight of the metering head, and a metering tool for taking up and dispensing substance, attached to the metering head. The metering tool is configured as a glass tubule having a glass punch slidably disposed therein, forming a seal. The metering head is provided with a first gripping tool for clamping the glass tubule in place and with a second gripping tool for clamping the glass punch in place. The metering head furthermore has a raising and lowering device for raising and lowering the second gripping tool relative to the first gripping tool, such that the glass punch can be raised and lowered in the glass tubule of the metering tool.

25 Claims, 12 Drawing Sheets

(51) Int. Cl.
  *B65D 83/42* (2006.01)
  *G01G 13/285* (2006.01)
  *G01N 35/10* (2006.01)
  *G01N 33/00* (2006.01)

(52) U.S. Cl.
  CPC ......... *G01G 17/06* (2013.01); *G01N 35/1072* (2013.01); *G01N 2033/0091* (2013.01); *G01N 2035/1039* (2013.01)

(58) Field of Classification Search
  CPC ........... G01N 2035/1039; B01L 3/0227; B01L 3/021–0213; G01G 17/06; G01G 13/2851; B65D 83/42
  USPC ..................................................... 73/864.13
  See application file for complete search history.

(56) References Cited

U.S. PATENT DOCUMENTS

| | | | | |
|---|---|---|---|---|
| 4,684,613 A | * | 8/1987 | Barrere | C12M 33/04 435/286.3 |
| 5,309,959 A | * | 5/1994 | Shaw | B65B 3/003 141/103 |
| 5,429,010 A | * | 7/1995 | Lohndorf | B25J 9/04 73/864.31 |
| 5,578,270 A | * | 11/1996 | Reichler | B01L 3/502 422/510 |
| 5,747,350 A | | 5/1998 | Sather | |
| 6,383,801 B1 | * | 5/2002 | Leighton | G01N 1/312 422/63 |
| 6,565,728 B1 | * | 5/2003 | Kozulic | B26D 7/1818 204/606 |
| 6,778,917 B1 | | 8/2004 | Jansen | |
| 6,805,175 B1 | * | 10/2004 | Pinkas | B65B 1/16 141/130 |
| 7,618,809 B2 | * | 11/2009 | Gebing | G01N 1/36 435/286.2 |
| 8,245,883 B2 | | 8/2012 | Luchinger et al. | |
| 2002/0146813 A1 | * | 10/2002 | Leighton | G01N 1/286 435/286.3 |
| 2004/0044439 A1 | | 3/2004 | Gueller et al. | |
| 2004/0245283 A1 | | 12/2004 | Kawanishi et al. | |
| 2005/0177134 A1 | * | 8/2005 | Gueller | G01G 13/2851 604/890.1 |
| 2009/0074622 A1 | * | 3/2009 | Kalamakis | B01L 3/0217 422/400 |
| 2010/0051648 A1 | * | 3/2010 | Luchinger | B65B 1/12 222/227 |
| 2010/0209303 A1 | * | 8/2010 | Tao | B01L 3/0275 422/523 |

FOREIGN PATENT DOCUMENTS

| | | |
|---|---|---|
| CN | 202433068 U | 9/2012 |
| DE | 102004035061 A1 | 2/2006 |
| EP | 1930702 A1 | 6/2008 |
| JP | 6307907 A | 11/1994 |
| JP | 200088716 A | 3/2000 |
| JP | 200088732 A | 3/2000 |
| JP | 2000234948 A | 8/2000 |
| JP | 200445308 A | 2/2004 |
| JP | 2004198166 A | 7/2004 |
| JP | 2004347513 A | 12/2004 |
| JP | 2007160296 A | 6/2007 |
| JP | 2008168274 A | 7/2008 |
| JP | 2010511573 A | 4/2010 |
| WO | 03098170 A1 | 11/2003 |

\* cited by examiner

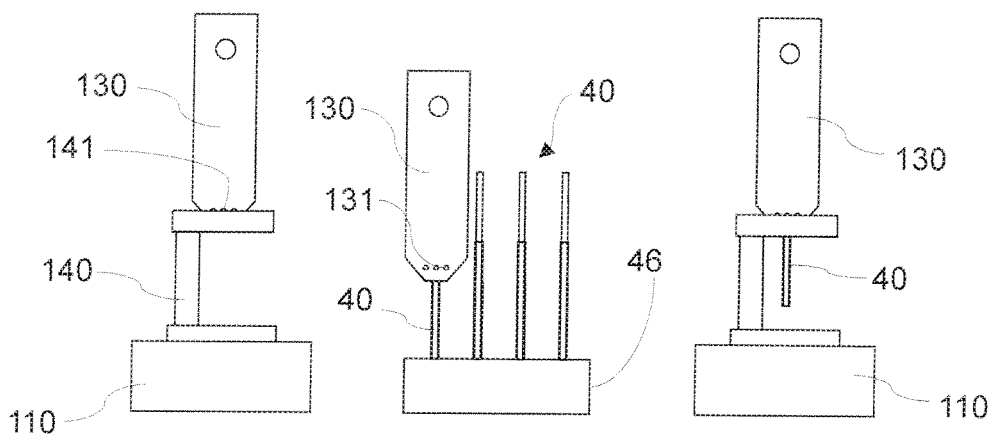
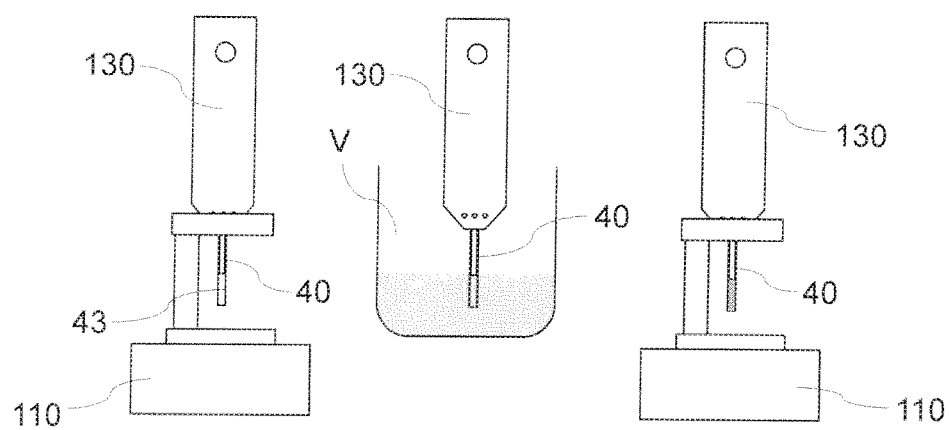
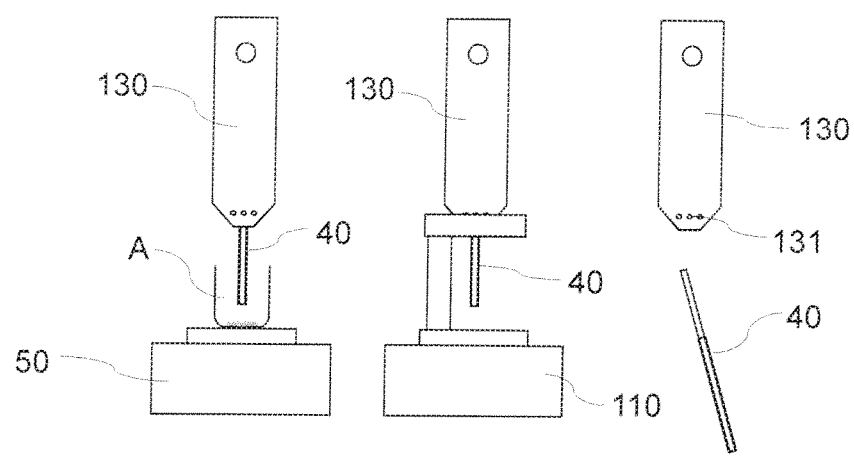

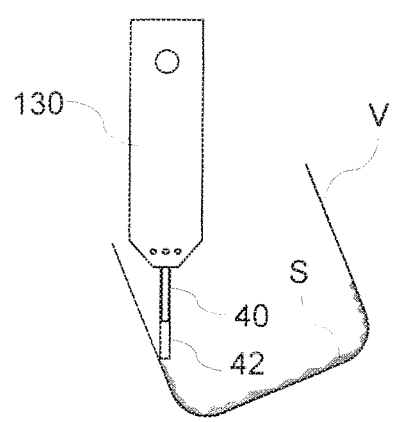
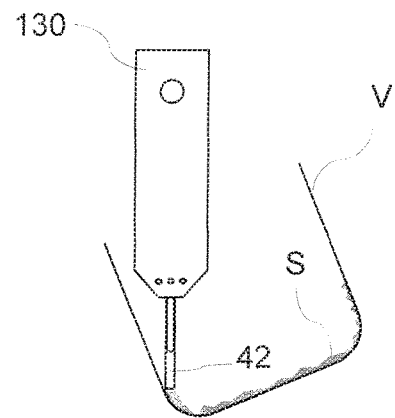
Fig. 15a  Fig. 15b
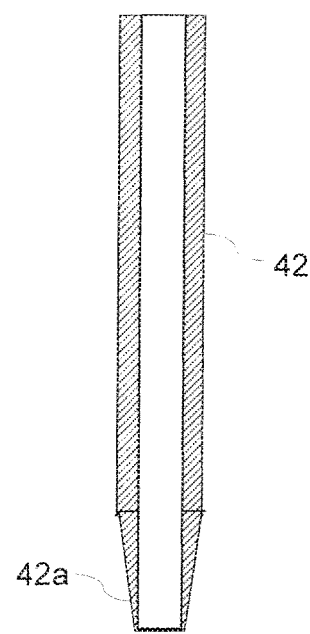
Fig. 16

METERING APPARATUS

CROSS-REFERENCE TO RELATED APPLICATIONS

This application is the United States national phase of International Application No. PCT/CH2015/000165 filed Nov. 9, 2015, and claims priority to Swiss Patent Application No. 1737/14 filed Nov. 10, 2014, the disclosures of which are hereby incorporated in their entirety by reference.

BACKGROUND OF THE INVENTION

Field of the Invention

The present invention relates to an apparatus for metering a substance, a metering method using the apparatus, and a metering tool for use in the apparatus.

Description of Related Art

A substance library or compound library or library of catalysts is the core of any chemical company, particularly in the pharmaceutical industry. Many compounds, often reflecting decades of synthesis activity, are filed here and form a source for many screening activities. The stored substances or compounds are often very valuable, difficult to synthesize, expensive to buy or to extract, and often the substances are only present in very small amounts worldwide.

Pharmaceutical companies often have a million and more substances on hand in their substance libraries and use their own substance management groups to administer them, which groups have the task of making required substance samples available from the library, often in tiny amounts all the way down into the sub-milligram range, for example for special biological tests. In this regard, the required substance amount must be removed from the storage container of the library and filled into a transport vessel (called 1:1 filling). Depending on the consistency or the physical properties of the substance to be filled into a container, this can only take place manually, up to the present, and therefore relatively great time expenditure and/or personnel effort is required, particularly at larger companies. Automation is difficult, among other things because the substances are often present in very different physical forms or consistencies. Furthermore, in the case of this manual method of procedure, there is always a significant contamination risk in the sense that traces of a substance from a prior metering process can get into the receptacle of a subsequent filling process (cross contamination). The extremely high metering precision that is often required, or the very slight substance amounts that are generally present and, accordingly, even smaller substance amounts to be dispensed, represent a further difficulty in practical work. A further practical difficulty consists in that the substances to be filled or metered can have very different consistencies, which require the use of specific filling tools, in each instance.

In WO 03/098170 A1, a computer-controlled metering apparatus is described, which is suitable for substances having practically any consistency (powder, liquid, oily, pasty, resinous). In one embodiment, the metering apparatus is equipped with a needle filling head, which is attached to an electronic scale, wherein the needle filling head, together with the scale, is mounted on a robot arm and can be moved in three dimensions by this arm. The needle filling head comprises a needle support, on which a plurality of metering needles in the form of tubules that are open in a downward direction are held in place in groups having different diameters from 0.1-5 mm. To pick up substance, the metering needles or tubules are immersed or inserted into the substance to be taken up, which is present in a storage container, by means of the robot arm, in defined manner, wherein depending on the diameter of the tubules, a different substance amount penetrates into the lower ends of the tubules and remains hanging there. Thereupon the needle filling head is raised and passed over the opening of the receptacle to be filled. Subsequently, pistons provided in the needle filling head are selectively introduced into the tubules from above, and thereby the substance situated in the tubules is ejected into the receptacle. In this regard, metering takes place step by step, i.e. emptying of the tubules begins with the tubule having the greatest diameter and continues toward tubules having a smaller diameter, until the desired metering amount is achieved within the scope of this step-by-step approximation. The substance amount metered into the receptacle during a metering step (emptying of a tubule), in each instance, is recorded by way of the scale, and the electronic controller causes step-by-step emptying of the further tubules if the desired metering amount has not yet been reached. In addition, a further scale having greater precision can be provided, on which scale the receptacle stands and with which scale precise recording of the actual metering amount is possible.

It is true that the metering apparatus known from WO 03/098170 A1 solves the problem of different substance consistencies, but it is not suitable or only suitable to a limited extent for filling small and tiny substance containers with take-up volumes in the milligram range or sub-milligram range. One reason for this lies in that such substance containers (called vials) are very small and normally are disposed tightly packed next to one another in holding racks (racks), and the substances are often present in such small amounts that often not even the bottom is covered or the substance sticks to the container walls. Because the openings of these vials are much too small to accommodate all the tubules of the needle filling head at the same time, the needle filling head would have to be moved for each individual metering process, in order to position the corresponding tubule precisely above the vial. In this process, however, at least some of the adjacent tubules, in each instance, would be situated above one or more of the other vials in the rack, and the risk of contamination of these vials is very high. A similar problem occurs due to the fact that the storage containers from which the substances to be filled into vials are taken must also have a certain minimum size, so that the tubules of the needle filling head can penetrate into them. In substance libraries, however, many substances are often present in such small amounts that the storage containers are simply too small for use of the known metering apparatus.

A further large problem lies in the inherent contamination risk as such. Because it cannot be definitely precluded that substance traces remain adhering in or to the tubules of the needle filling head, the tubules must be replaced, in each instance, before a different substance is metered. However, this is relatively labor-intensive. Alternatively, of course, the needle metering head or its needle support as a whole could also be replaced. But this would also be complicated and above all would require keeping a large number of needle filling heads or needle supports on hand, and this would be undesirable for economic reasons.

SUMMARY OF THE INVENTION

By means of the present invention, a metering apparatus is now supposed to be made available, which avoids the disadvantages of the known metering apparatuses as described. In more concrete terms, a cost-advantageous solution for a metering apparatus is supposed to be indicated, which is suitable for substances of practically any consistency, can meter even the smallest substance amounts down into the milligram and sub-milligram range, with sufficient precision, and with which contamination problems are reliably avoided without special effort. Further objects of the invention consist in making a metering method available, using the metering apparatus, and in making a metering tool available for use in the metering apparatus.

These objects on which the invention is based are accomplished by the apparatus according to the invention disclosed herein.

With regard to the metering apparatus, the essence of the invention consists of the following: An apparatus for metering a substance comprises a metering head and a metering tool releasably attached to the metering head for taking up and dispensing substance. The metering tool is configured as an essentially cylindrical tubule having a punch disposed in it, which punch slides adjustably, essentially forming a seal, wherein the punch is longer than the tubule and projects out of the tubule at its upper end. The metering head is provided with a first gripping tool that can open and close for releasable clamping of the tubule, and with a second gripping tool that can open and close for releasable clamping of the punch. Furthermore, the metering head is provided with a raising and lowering device, by means of which the second gripping tool can be raised and lowered relative to the first gripping tool, and thereby the punch can be raised and lowered in the tubule. It is very particularly advantageous if the tubule and the punch consist of glass.

By means of the formation of the metering tool as a tubule having an integrated punch, on the one hand substances of practically any consistency can be metered, and on the other hand, the contamination problem is completely eliminated, because the metering tool can be produced in such cost-advantageous manner, due to its extremely simple design, that it can be disposed of after every use.

According to a first advantageous embodiment, the metering head has an internal controller for the raising and lowering device as well as for the first and the second gripping tool, and operating elements that work together with the internal controller. As a result, the metering head can be used as an autonomous hand-held device.

Advantageously, in this regard, the internal controller has an interface for communication with an external controller and/or for an external charging current source.

Expediently, the apparatus has a scale for the metering head and the scale is provided with a holder for the metering head. In this way, the metering head can simply be placed on the scale.

Advantageously, in this regard, the holder is equipped with electrical contacts, which are configured for working together with corresponding electrical contacts on the metering head. In this way, a communication connection with the scale can be produced in simple manner, and preferably, charging of a rechargeable battery provided in the metering head as a power supply can also take place.

According to a second advantageous embodiment, the apparatus has a scale, and the metering head is disposed on the scale in such a manner that the scale measures the weight of the metering head (with or without substance taken up in it).

According to an advantageous further development, the metering head is equipped with a second raising and lowering device, by means of which the first gripping tool can be raised and lowered, together with the first raising and lowering device for the second gripping tool as mentioned. By means of this second raising and lowering apparatus, a more sensitive movement of the metering tool is possible than when moving the entire metering head.

Expediently, the scale is attached to a robot arm, wherein the metering head can be adjusted by means of the robot arm, specifically preferably in all three spatial directions.

Expediently, the apparatus is equipped with control electronics for the scale and the raising and lowering device as well as the first and the second gripping tool. The metering apparatus can be operated automatically by means of the control electronics.

Advantageously, the metering apparatus is provided with a further scale for weighing a substance receptacle that holds the substance being dispensed. With this further scale, which preferably demonstrates greater precision than the first scale, the actual metered substance amount can be controlled and measured precisely.

Expediently, the (glass) tubule has an inside diameter in the range of 0.1 to 5 mm, preferably 0.1 to 2 mm, even more preferably 0.1 to 1 mm.

Furthermore, it is advantageous if the punch is configured as a glass rod or as a glass tube that is closed at least on one side.

According to a particularly advantageous embodiment, the (glass) tubule has a wall thickness in the range of 0.03 to 0.2 mm, preferably 0.03 to 0.1 mm. In addition or alternatively, the (glass) tubule has an end configured as a sharp edge or in the manner of a blade.

According to a further advantageous embodiment, the apparatus has rotation means, which rotate the metering tool about its longitudinal axis while it is being raised and lowered by the second raising and lowering device.

According to a further advantageous embodiment, the apparatus has a rack for a number of at least partially different or differently dimensioned metering tools.

With regard to the metering tool, the essence of the invention consists in the following: A metering tool for use in a metering apparatus is configured as an essentially cylindrical tubule having a punch disposed in it to slide adjustably, essentially forming a seal, wherein the punch is longer than the tubule and projects out of the tubule at one of its ends, and preferably does not fill the tubule completely, so that a metering chamber remains free at the other end of the tubule.

The metering tool, which particularly advantageously consists entirely of glass and is composed of only two parts, can be produced in very cost-advantageous manner because of its design simplicity, and, therefore, can be disposed of after every metering process, so that contamination problems are avoided practically completely.

According to another advantageous embodiment, the (glass) tubule is configured to be cylindrical and has an inside diameter in the range of 0.1 to 5 mm, preferably 0.1 to 2 mm, even more preferably 0.1 to 1 mm. With these dimensions, metering amounts of several hundred mg to down into the sub-milligram range can be implemented.

Preferably, the punch is configured as a glass rod or as a glass tube closed at least on one side. This leads to simple producibility of the punch.

Preferably, the (glass) tubule has a wall thickness in the range of 0.03 to 0.2 mm, preferably 0.03 to 0.1 mm. By means of these relatively small wall thicknesses, the free edge of the (glass) tubules more or less acts as a blade, which promotes immersion or, more precisely, insertion into substances having a firmer consistency, as well as scraping or scratching substance off a container wall. In addition or alternatively, the (glass) tubule has an end configured as a sharp edge or in the manner of a blade.

With regard to the metering method, the essence of the invention consists of the following: A method for metering a substance, using the apparatus according to the invention, comprises the following steps:

clamping the metering tool into the metering head by means of opening and closing the gripping tools, positioning the metering tool above a substance storage container, lowering the metering tool to immerse or insert the metering tool into a substance situated in the substance storage container, and thereby taking up substance into a substance chamber of the metering tool, preferably with monitoring by a scale, raising the metering tool, if applicable, lowering the punch of the metering tool relative to the tubule to eject excess substance, preferably with monitoring by a scale, positioning the metering tool above a substance receptacle, and lowering the punch of the metering tool relative to the tubule to completely eject substance out of the metering tool into the substance receptacle.

At the end of metering, the metering tool can be ejected from the metering head by opening the gripping tools.

Advantageously, the metering is carried out in individual partial metering steps, wherein, preferably with monitoring by a scale, step-by-step approximation to a required target metering amount takes place.

Expediently, the substance amount taken up by the metering tool is trimmed with monitoring by a scale.

Advantageously, the actual amount of the substance metered into the substance receptacle is measured by means of a (further) scale.

Very particularly preferably, the metering tool is rotated about its longitudinal axis during immersion or insertion into a substance situated in the substance storage container, and preferably also during its retraction from the substance. The rotation movement facilitates insertion in the case of substances having a relatively firm consistency. Furthermore, it prevents sticking of the metering tool in the substance, and allows removing a substance plug in the case of certain substances.

Advantageously, a number of metering tools that are at least partially different or are dimensioned differently are made available preferably in a rack, and the metering tool to be clamped is selected from these metering tools that are made available. In this manner, different metering amounts from several hundred mg down to far into the sub-milligram range can be achieved by means of a corresponding selection of the metering tools.

BRIEF DESCRIPTION OF THE DRAWINGS

In the following, the invention will be explained in greater detail using exemplary embodiments shown in the drawing. The figures show.

DESCRIPTION OF THE INVENTION

Figure 1:
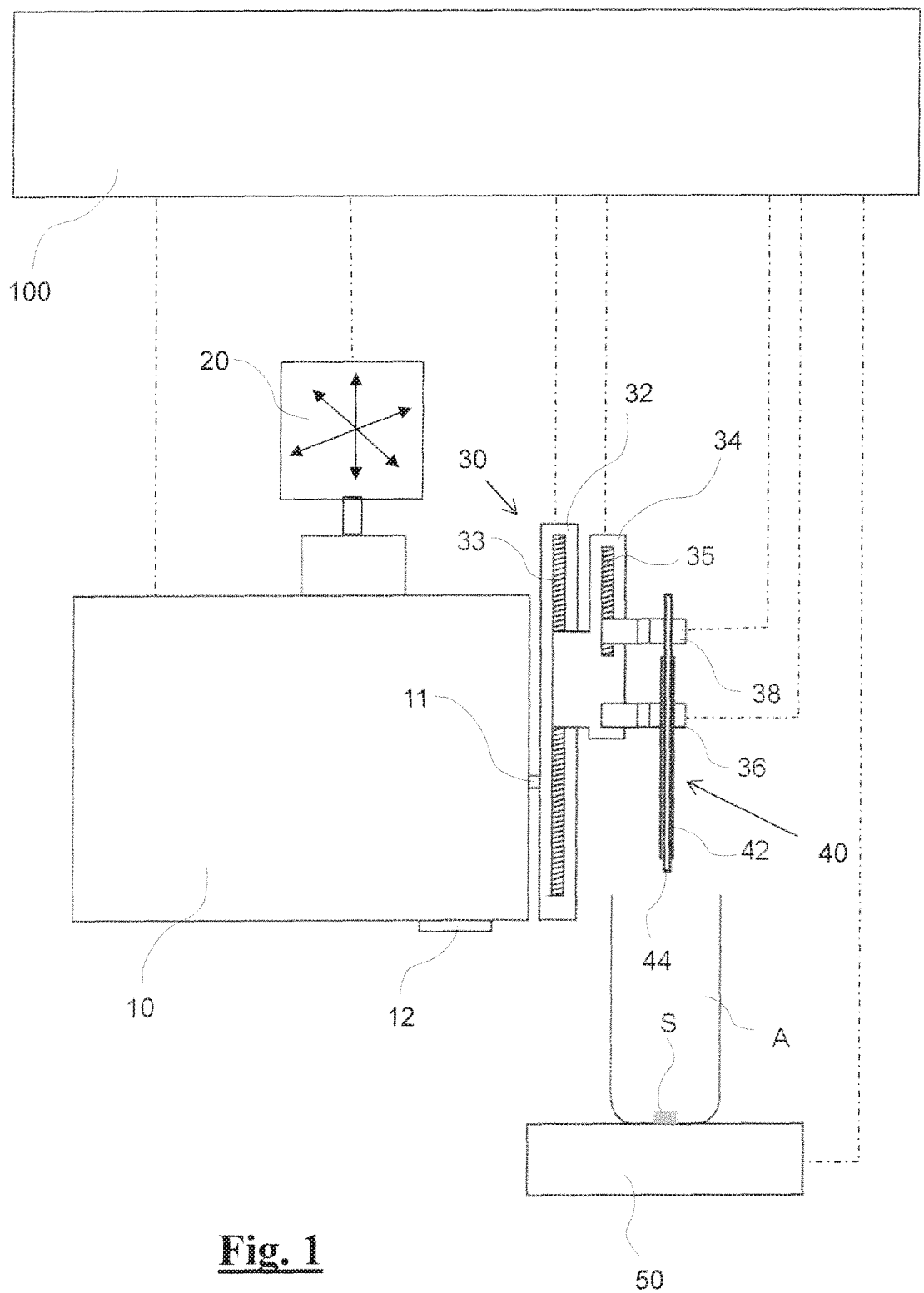
FIG. 1—a schematic representation of a first exemplary embodiment of a metering apparatus according to the invention, FIG. 2—a schematic horizontal section through a gripping tool of the metering apparatus, FIGS. 3-8—each a schematic representation of the metering apparatus according to FIG. 1 in different phases of a metering process, FIG. 9a-d—each a metering tool of the metering apparatus according to FIG. 1 in different phases of a metering process, FIG. 10a-d—each a metering tool of the metering apparatus according to FIG. 1 in different phases of the metering of liquids, FIG. 11a-b—two variants of the metering head with metering tool of a second exemplary embodiment of a metering apparatus according to the invention, FIG. 12a-c—each a schematic sectional representation of the metering head with metering tool according to FIG. 11a in different phases of a metering process, FIG. 13a-i—each a schematic representation of the metering apparatus having a metering head with metering tool according to FIG. 11a in different phases of a metering process, FIG. 14a-e—a metering head with metering tool of a third exemplary embodiment of a metering apparatus according to the invention in different phases of a metering process, and FIG. 15a-b—two schematic drawings to explain how crystallized substances are picked up, and FIG. 16—an axial section through a modified tubule of the metering tool of the metering apparatus.

The following statement applies to the description below: If reference signs are indicated in a figure for the purpose of clarity of the drawing but not mentioned in the directly related description part, reference is made to their explanation in preceding or subsequent description parts. Vice versa, in order to avoid overloading the drawing, reference signs that are less relevant for direct understanding are not entered in all the figures. Reference is made to the other figures, in each instance, for this purpose.

The first exemplary embodiment of the metering apparatus shown in FIG. 1 comprises an electronic scale 10, which is releasably mounted on a robot arm 20, indicated merely symbolically with a box. Control electronics 100 are provided to control the robot arm 20. The scale 10 can be moved in all three spatial directions by means of the robot arm 20, within the reach of the robot arm.

On the scale 10, a metering head referred to as a whole as 30 is mounted on a weighing arm 11 that is connected with the weighing cell in the interior of the scale, in such a manner that the scale measures the weight of the metering head 30 and of all the components attached to it or carried by it. An adjustable locking element 12 is provided on the scale 10 to protect it, which element fixes the metering head 30 in place relative to the scale 10 if no weighing is required at a specific time, see for example FIG. 3. The scale can also be locked when it is being moved and/or set up.

To this extent and in this general way, the metering apparatus according to the invention does not differ from the known metering apparatus according to the document WO 03/098170 A1 that has already been mentioned, so that a person skilled in the art does not require any further explanation in this regard.

The metering head 30 essentially comprises a first raising and lowering device 32 and a second raising and lowering device 34, which is mounted on the first raising and lowering device 32 and can be raised and lowered by means of it (vertically in the position of use of the metering apparatus). A first gripping tool 36 is mounted, fixed in place, on the second raising and lowering device 34. A second gripping tool 38 is disposed on the second raising and lowering device 34, in such a manner that it can be raised and lowered by means of it (vertically in the position of use of the metering apparatus) relative to the first gripping tool 36. For the raising and lowering movement of the two gripping tools 36 and 38, the two raising and lowering devices 32 and 34 are equipped with threaded spindles 33 and 35, driven to rotate by motors not shown. Of course, the raising and lowering devices 32 and 34 can also be implemented in a different way.

Figures 9A, 9B, 9C, 9D:
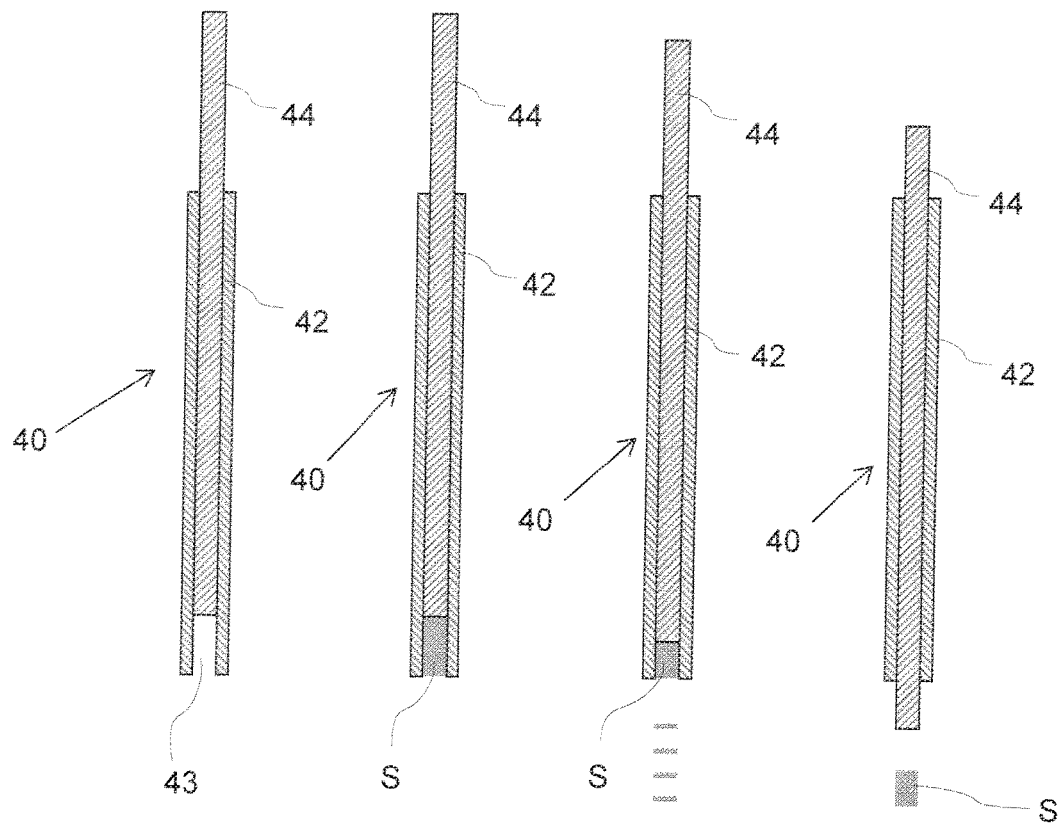

For the actual substance metering, in other words taking up substance from a storage container and dispensing substance into a substance receptacle, a specifically configured metering tool 40 is provided. As shown on a larger scale in FIG. 9a, this metering tool 40 consists of two parts, preferably of an essentially cylindrical glass tubule 42 and of a punch 44 that also consists of glass. The glass punch 44 is slightly longer than the glass tubule 42 and projects out of the upper end of the glass tubule 42. Vice versa, the glass punch 44 (in the starting state) does not extend over the entire length of the glass tubule 42, but rather leaves a metering chamber 43 of the glass tubule 42 open (FIG. 9a). Alternatively, the metering chamber 43 can also be formed only during the metering process, by pulling the glass punch 44 out of the glass tubule 42 to a limited extent, wherein the size or the volume of the metering chamber can be adjusted in accordance with the respective requirements.

The cross-section of the glass punch 44 is adapted to the inside cross-section of the glass tubule 42, so that the glass punch 44 acts as a piston. The glass punch 44 can be configured as a solid glass rod or as a glass tube that is closed at least at its end that lies within the glass tubule 42. Furthermore, the glass punch can fundamentally also be configured in the form of a glass piston disk and a glass piston rod.

The metering tool 40 can fundamentally also be formed of a material other than glass, for example of plastic. However, glass is chemically inert in practically all cases, and also demonstrates a certain elasticity in the case of suitable dimensions. In the following, the invention will therefore be described throughout using a metering tool that consists of glass.

During use of the metering apparatus according to the invention, the metering tool 40 is held in place at its glass tubule 42 by the first gripping tool 36. The second gripping tool 38 holds the glass punch 44 in place.

Figure 2:
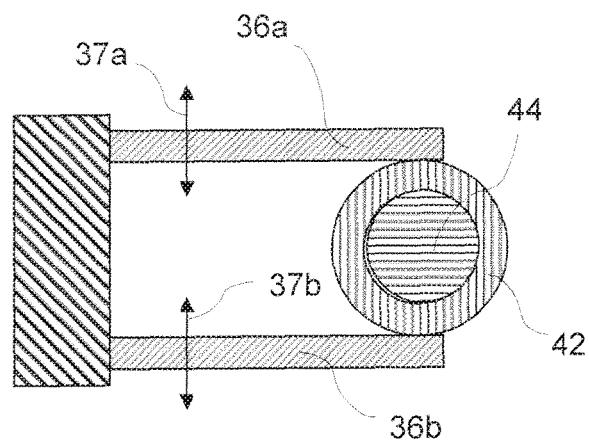

As can be taken from FIG. 2, the first gripping tool 36 essentially comprises two clamping jaws 36a and 36b, which clamp the glass tubule 42 of the metering tool 40 in place between them. The two clamping jaws 36a and 36b can be moved away from one another and toward one another by means of a drive indicated here only by means of arrows 37a and 37b.

The second gripping tool 38 is configured analogous to the first gripping tool 36 and therefore not represented separately.

FIG. 1 furthermore also shows a substance receptacle A, which stands on a second electronic scale 50. Advantageously, the second scale is an analysis scale, the resolution and precision of which are at least as great, preferably greater than the resolution and precision of the first scale 10. Advantageously, the precision of the second scale 50 is about 0.01 mg, preferably even about 0.001 mg.

The first scale 10, the two raising and lowering devices 32 and 34, the two gripping tools 36 and 38, and the second scale 50 are controlled by the control electronics 100 in terms of their function. Practical implementation of the required functions (reading the scales, moving the robot arm, moving the raising and lowering devices, closing and releasing the gripping tools) lie within the normal range of knowledge of a person skilled in the art of controls, and therefore do not require any more detailed explanation.

In the following, a metering method carried out using the metering apparatus according to the invention will be described in greater detail, using FIGS. 3-9d.

Figure 3:
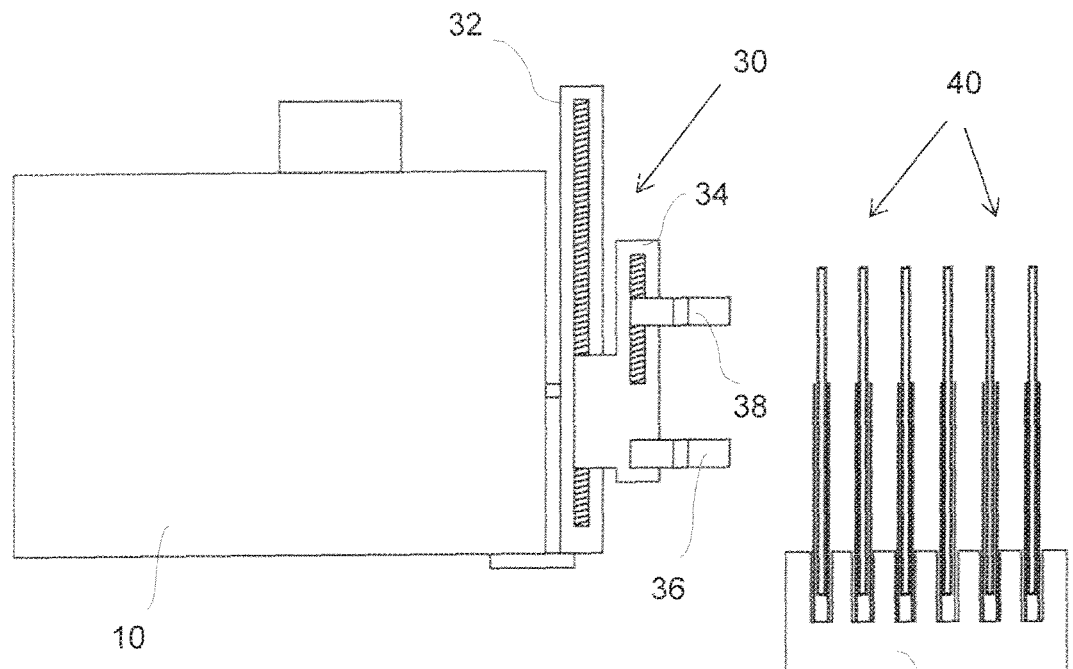
Figure 4:
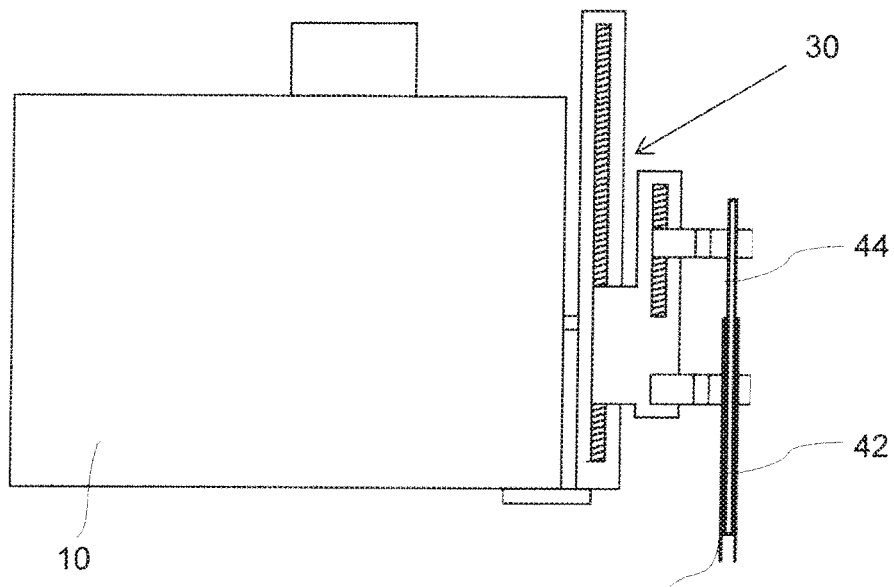

In the starting state shown in FIG. 3, there is as yet no metering tool 40 on the metering head. A number of metering tools 40 is kept on hand in a holding rack (rack) 46. By means of the robot arm 20, the metering head 30 is moved up to the rack 46, and the two gripping tools 36 and 38 grip a metering tool 40 and hold it in place. The metering tool 40 is then removed from the rack 46 by moving the robot arm 20 (FIG. 4). Of course, vice versa, the rack 46 could also be moved up to the metering head 30 by means of a different transport apparatus and then moved away again.

Figure 5:
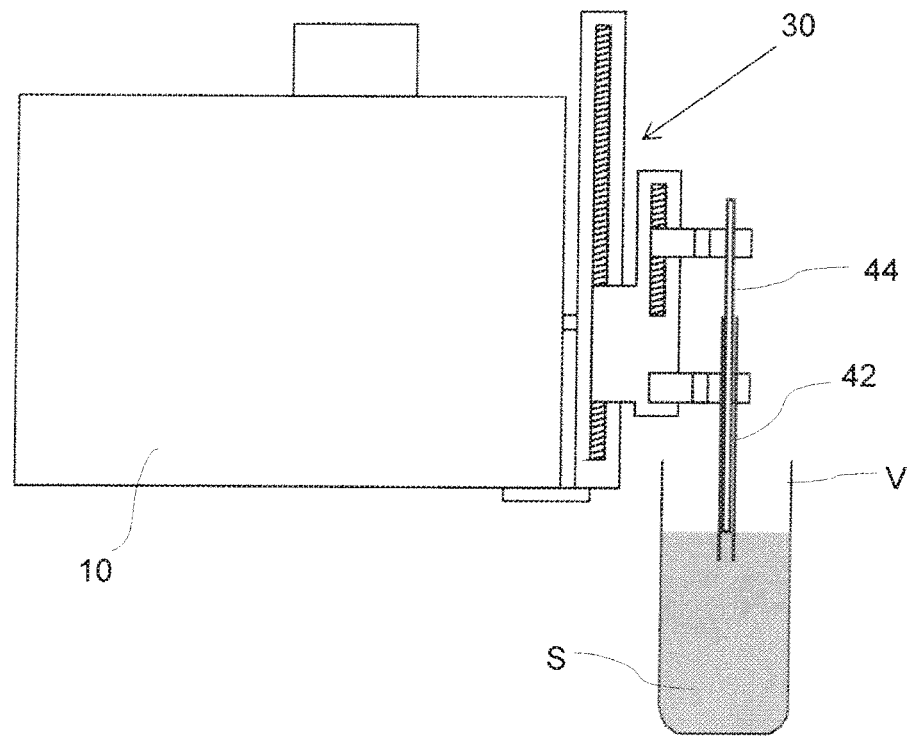

Subsequently, the metering tool 40 is positioned, by means of the robot arm 20, above a storage container V that has been made available and contains the substance to be metered, and then lowered until the glass tubule 42 of the metering tool 40 is immersed in the substance S, or, depending on the consistency of the substance, stabs into it (FIG. 5). During this process, the metering chamber 43 of the glass tubule 42 is filled with substance S (FIG. 9b). If applicable, the glass punch 44 is previously pulled slightly out of the glass tubule 42 to form the metering chamber 43, by means of the second raising and lowering device 34.

Figure 6:
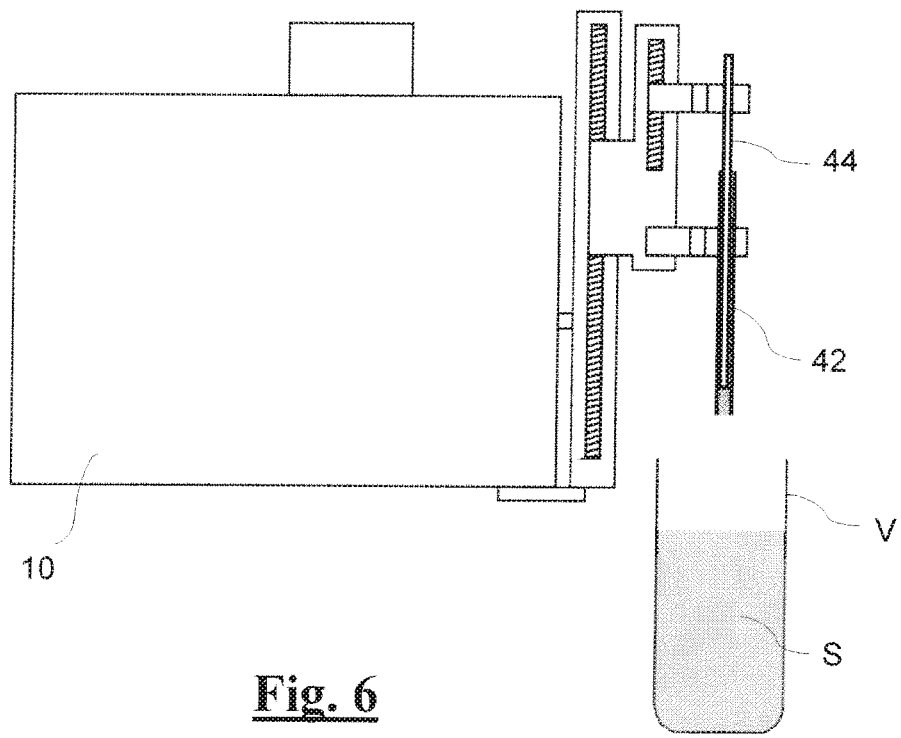

Thereupon the metering tool 40 is raised above the edge of the storage container V by means of the first raising and lowering device 32 (FIG. 6). Possible substance parts projecting out of the lower end of the glass tubule 42 are previously stripped off by means of a sideways movement of the metering head 30. Using the first scale 10, the amount (weight) of the substance S taken up by the metering tool 40 in this manner is measured. If the substance amount taken up is greater than a predetermined nominal metering amount, the excess substance amount is ejected out of the glass tubule 42 back into the storage container V with monitoring by the first scale 10. For this purpose, the glass punch 44 is lowered by means of the second raising and lowering device 34, relative to the glass tubule 42 held stationary in the first raising and lowering device 32, until the first scale 10 detects a specific substance amount. This trimming of the metering amount by ejection of the excess substance amount is shown in FIG. 9c. Trimming can also take place iteratively, in multiple steps (feedback loop).

Figure 7:
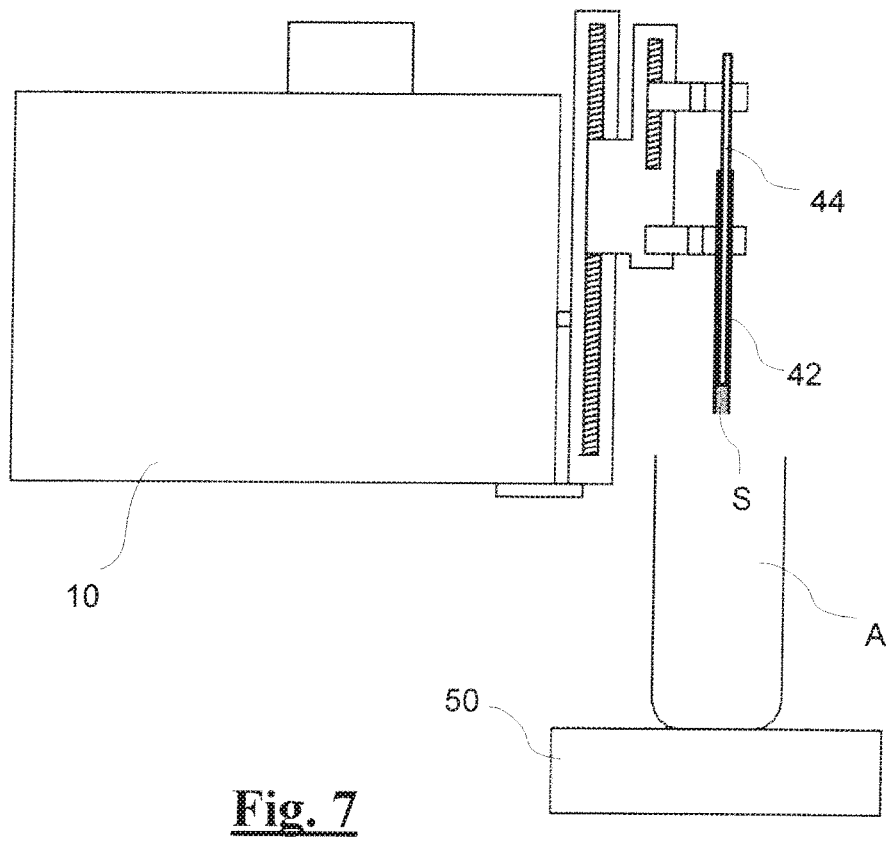

Now the metering head 30, with the metering tool 40 held in it, is moved by means of the robot arm 20 above a substance receptacle A that is made available on the second scale 50, into which receptacle the substance S is to be metered (FIG. 7). The substance receptacle A often is a very small container (vial), which, together with many other substance receptacles, is disposed in a holding rack (rack) in matrix form.

Figure 8:
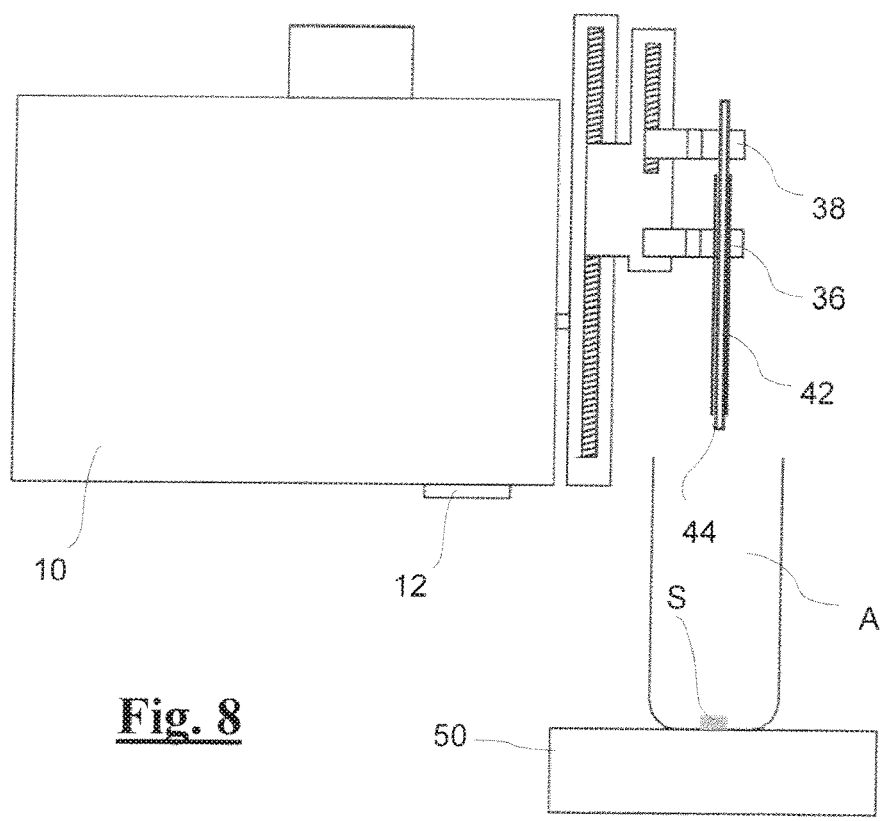

Subsequently, the glass punch 44 of the metering tool 40 is moved downward by means of the second raising and lowering device 34, while the glass tubule 42 is held stationary by means of the first gripping tool 36, and thereby the substance amount contained in the glass tubule 42 is ejected from the glass tubule 42 into the substance receptacle A (FIG. 8 and FIG. 9d). The substance amount actually metered in can be controlled by means of the second (more precise) scale 50. The actual metering amount can also be recorded in suitable manner and then be assigned to the filled substance receptacle. In most cases, it is sufficient if metering itself is only somewhat precise, but the actual metering amount is known in highly precise manner. As seen in FIG.

9d, the punch 44 is slidable to project out of the tubule 42 at both of the tubule ends simultaneously.

If a further substance receptacle A is supposed to be filled with the same substance or if the substance amount metered in this manner has not yet reached the required substance amount, the method cycle just described is repeated in accordance with FIGS. 5-8 (immersion, trimming, ejection).

If another substance is supposed to be filled, first the metering head 30 is positioned above a waste container and the metering tool 40 is disposed of there (discarded). For this purpose, the gripping tools 36 and 38 are simply opened, so that the metering tool 40 falls downward into the waste container. Subsequently, a new metering tool 40 is once again picked up from the rack 46 (FIG. 4), and metering of the next substance takes place once again in accordance with the method sequence described above using FIG. 5-8 (immersion, trimming, ejection).

The sequences described above, as has already been mentioned, are controlled by the control electronics 100. The programmable control electronics are configured for carrying out the following procedures for this purpose:
- moving the metering head in preferably three spatial directions by means of the robot arm 20,
- clamping a (selected) metering tool 40 into the metering head 30 by means of opening and closing the gripping tools 36 and 38,
- positioning the metering tool 40 over the substance receptacle V,
- lowering the entire metering head 30 or, alternatively, only the metering tool 40, to immerse the metering tool 40 into the substance S contained in the substance storage container, and thereby taking up substance into the metering tool,
- raising the metering tool 40, preferably by means of the first raising and lowering device 32,
- reading the first scale 10 and, if applicable, the second scale 50, and evaluating the measurement results of the scale(s),
- lowering the glass punch 44 of the metering tool 40 relative to the glass tubule 42 by means of the second raising and lowering device 34, to eject excess substance, with monitoring by the first scale 10, if applicable iteratively,
- positioning the metering tool 40 above the substance receptacle A,
- lowering the glass punch 44 of the metering tool 40 relative to the glass tubule 42 by means of the raising and lowering device 34, for complete ejection of substance from the metering tool 40 into the substance receptacle A,
- ejection of the metering tool 40 from the metering head 30 by means of opening the gripping tools 36 and 38.

Preferably, a great number of metering tools 40 is kept on hand in the rack 46. Advantageously, metering tools having different dimensions or clear widths (inside diameters) of their glass tubule 42 are present. The inside diameters can lie in a range of 0.1 mm to about 5 mm, for example, preferably with a gradation of about 0.5 mm, for example. Preferably, the inside diameters lie in a range of 0.1 to 2 mm, specifically in a range of 0.1 to 1 mm. In this manner, different metering amounts from several hundred mg down to far into the sub-milligram range can be achieved by means of a suitable selection of the metering tools. Because the programmable control electronics 100 know how great the required metering amount is supposed to be, by means of suitable input, they can automatically select suitable metering tools 40 in targeted manner. Furthermore, the volume capacity of the metering chamber can be adapted by means of adjusting the glass punch in the glass tubule of the metering tool.

However, use of metering tools 40 having different diameters of the glass tubules 42 has yet a further advantage in that rapid iterative approximation to the required reference metering amount, in each instance, can be implemented very easily in this way. In this regard, first one or more metering passes are carried out with the largest possible metering tool. The largest possible metering tool is understood, in this regard, to be one having a glass tubule 42 designed for a nominal metering amount that comes as close as possible to the required target metering amount but does not exceed it. By means of the first scale 10 and/or the second scale 50, the residual metering amount still required is determined after every metering pass. If the residual amount is smaller than the nominal metering amount of the metering tool just used, this tool is discarded and a new, next smaller metering tool is used, the nominal metering amount of which does not exceed the residual metering amount. With this, metering passes are now carried out until the remaining residual metering amount is once again smaller than the nominal metering amount of the metering tool used. This process is continued with increasingly smaller metering tools, in other words metering tools having smaller diameters of their glass tubules 42, until the required target metering amount has been reached within a predetermined tolerance. Instead of selecting a smaller metering tool, if applicable, the holding capacity of the metering chamber of the metering tool can also be adapted accordingly.

For a great metering precision, it is important that the glass punches 44 slide in the glass tubules 42 of the metering tools 40 with the most precise fit possible (in tight manner). A precision (play) of about 0.01 mm should be aimed at. The wall thicknesses of the glass tubules 42, as a function of their diameter, preferably typically amount to about 0.03 to about 0.2 mm, preferably about 0.03 to about 0.1 mm. The lengths of the glass tubules 42 typically amount to about 70 mm; the lengths of the glass punches 44 are slightly greater, typically about 80 mm.

The shape of the tubule 42 imparts relatively great rigidity to it, in spite of its thin walls, and this rigidity is important for insertion into firm(er) substances or more compact powders. The thin walls are also important for piercing. In addition or alternatively, an end 42a of the tubule 42 can also be sharpened or configured like a blade, as shown in FIG. 16. Furthermore, it can also be advantageous to configure the immersion end or piercing end of the tubule 42 so as to widen (slightly) toward the outside.

With every change of the metering tools 40, either because a different dimension of the glass tubule is required or because a different substance is to be metered, the metering tool previously used is discarded, in other words no longer used. In this way, contamination problems are avoided with the greatest possible reliability. The metering apparatus according to the invention allows this concept by means of the use of specially configured metering tools 40 that consist entirely of glass and are the only parts of the entire metering apparatus that come into contact with the substances to be filled. The metering tools 40 consist only of two simple glass components (glass tubule 42 and glass punch 44), which can be produced in simple and cost-advantageous manner as mass-produced items, so that their use as disposable parts is economically justifiable.

Figures 10A, 10B, 10C, 10D:
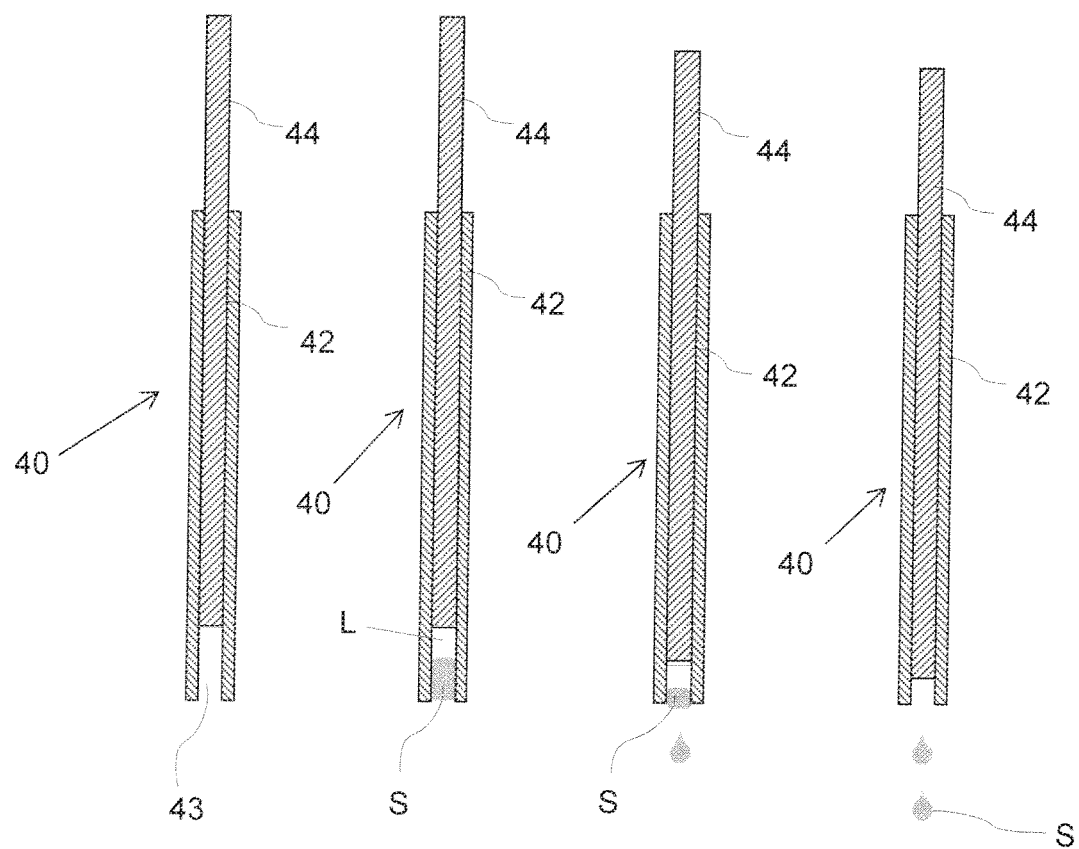

FIGS. 10a-d show a particularity during pickup and dispensing of a liquid substance into and out of the metering tool 40. FIG. 10a corresponds to FIG. 9a. FIG. 10b shows the metering tool 40 in the state in which it is immersed into the substance S to be taken up. In the metering chamber 43, there is an air cushion L between the glass punch 44 and the liquid plug S. FIGS. 10*c* and 10*d* show how the substance S can be ejected from the metering chamber 43 droplet by droplet, by means of surge-like lowering of the glass punch 44. In this regard, the glass punch is moved very rapidly and thereby generates pressure pulses that eject the liquid substance droplet by droplet.

In the method sequence described above, the first scale serves as a decision scale (Was a sufficient substance amount taken up?) and the second scale serves as an actual measurement scale (What substance amount was effectively metered in?).

In the following, a somewhat simpler embodiment of the metering apparatus according to the invention will be explained using FIGS. 11*a*-*b*, 12*a*-*c*, and 13*a*-*i*. The most fundamental difference as compared with the embodiment described above consists in that the metering head of the metering apparatus is configured as an independent element that must be moved manually. The following description is therefore essentially restricted to the configuration of the metering head as well as to a method sequence given as an example, with the use of such an independent metering head.

Figure 11A:
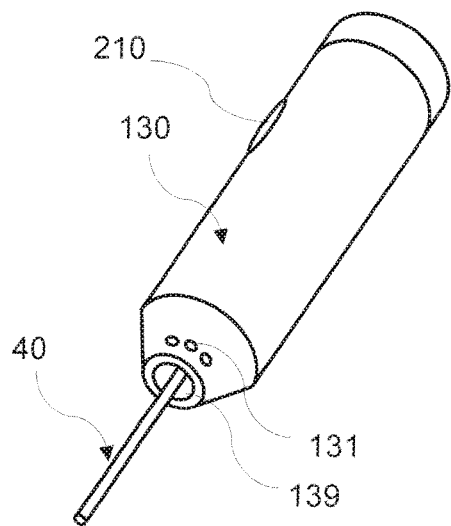
Figure 11B:
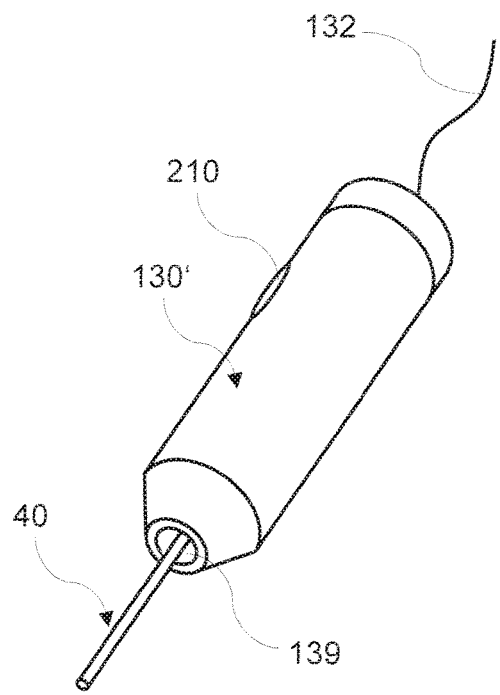
Figures 12A, 12B, 12C:
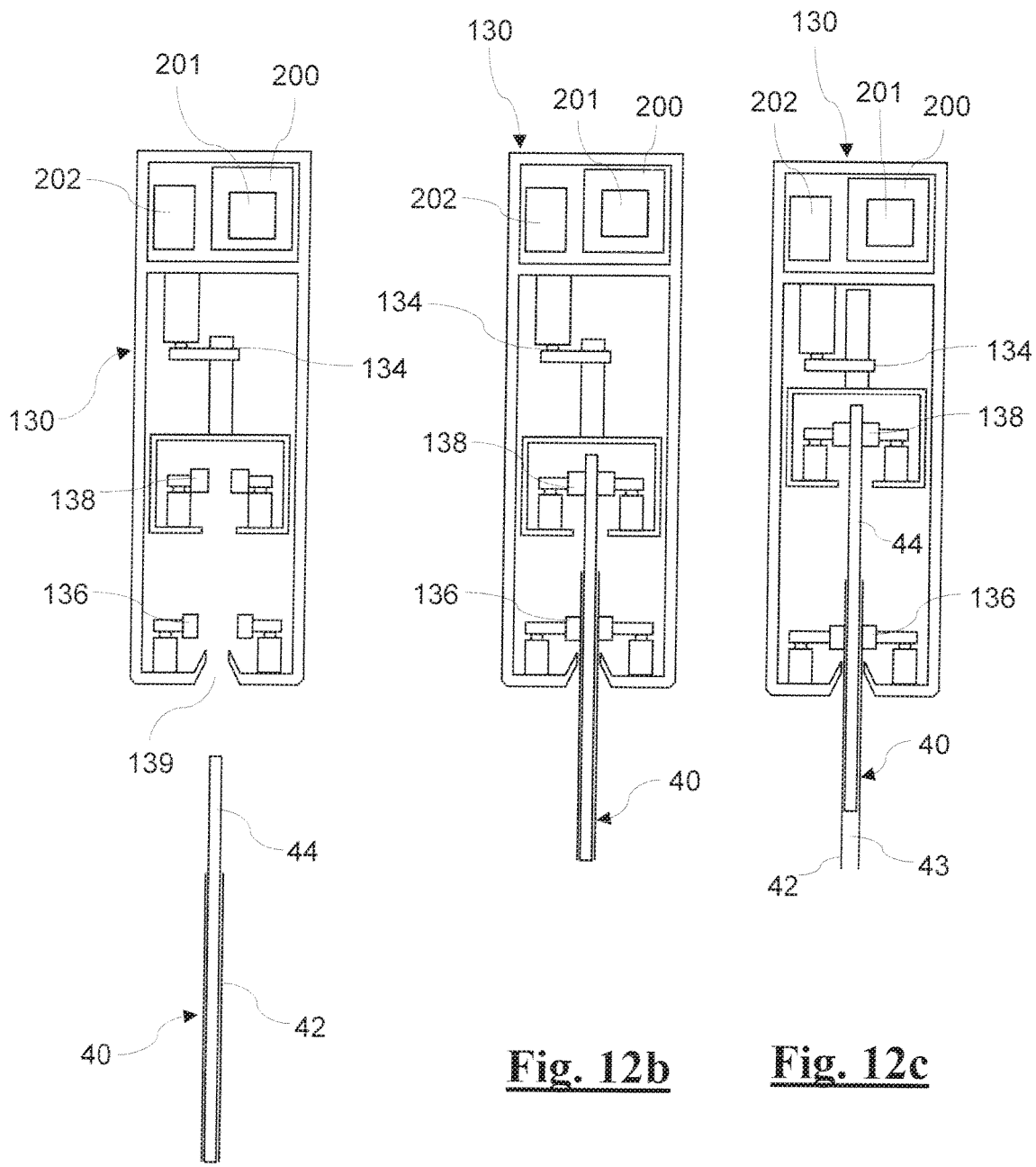

FIGS. 11*a* and 11*b* show two variants of a metering head 130 and 130'. In both variants, the metering head has an essentially cylindrical outer shape, for example. In the variant of FIG. 11*a*, electrical contacts 131 are provided on the metering head 130, by way of which contacts electrical components situated in the metering head can be connected with external components, for example a scale or an overriding controller or a charging current source. In the variant of FIG. 11*b*, the electrical connection of the metering head 130' toward the outside takes place by way of a cable 132. In a third variant, not shown, a wireless connection could also be provided. In these variants, operating elements 210 are provided on the metering head 130 or 130', on the outside, which elements work together with an internal controller 200 situated in the metering head (FIG. 12*a*). The operating elements 210 can be configured, for example, in the form of a known function switching button having multiple switching functions, for example.

On one of its face sides, the metering head 130 or 130' is provided with a conically configured guide opening 139, through which a metering tool 40 can be inserted into the metering head. More details in this regard are explained below.

The inner structure of the metering head 130 is evident from FIG. 12*a*. The metering head 130 comprises a first gripping tool 136, a second gripping tool 138, and a raising and lowering device 134 for the second gripping tool 138. Furthermore, the metering head 130 comprises the internal controller 200 that has already been mentioned, as well as a chargeable power source or a rechargeable battery 202. In the metering head 130', the power supply can be provided by way of the cable 132, so that the rechargeable battery is not absolutely necessary.

The two gripping tools 136 and 138 and the raising and lowering device 134 are fundamentally the same, in terms of design and function, as the corresponding components of the first exemplary embodiment of the metering apparatus, and therefore require no further explanation. The two gripping tools 136 and 138 and the raising and lowering device 134 are controlled by the internal controller, wherein opening and closing of the gripping tools and raising and lowering of the second gripping tool relative to the first gripping tool is triggered manually by way of operating elements 210 connected with the internal controller 200.

The internal controller 200 is equipped with an interface 201, which serves for communication with the outside. The interface 201 is either connected to the electrical contacts 131 or to the cable 132. Alternatively, the interface can also be structured as a wireless connection. FIG. 12*a* shows the metering head 130 in a position above a metering tool 40, wherein the two gripping tools 136 and 138 are open. In FIG. 12*b*, the metering head 130 is set onto the metering tool 40 or the latter is introduced into the metering head 130, wherein the two gripping tools 136 and 138 are closed and hold the metering tool 40 in place. In FIG. 12*c*, the second gripping tool 138 is displaced slightly upward by means of the raising and lowering device 134, and thereby the glass punch 44 of the metering tools 40 is pulled slightly out of the glass tubule 42, and therefore a metering chamber 43 has been formed at the lower end of the metering tool 40.

FIGS. 13*a*-13*i* illustrate the individual phases of a typical metering process when using the metering head 130.

At the beginning, the metering head 130 is weighed by means of a scale 110. The scale 110 is equipped with a holder 140, into which the metering head 130 can be inserted. The holder 140 is equipped with electrical contacts, which contact the electrical contacts 131 of the metering head 130 when the metering head 130 is inserted into the holder 140. In this regard, the rechargeable battery 202 in the metering head 130 can be charged or a weighing process can be triggered (by way of the function switching button 210).

After the weighing process, the metering head 130 is equipped with a metering tool 40. For this purpose, the metering head 130 is manually guided above a holding rack (rack) 46 and then set onto a selected metering tool 40 (FIG. 13*b*). Clamping of the metering tool 40 is then triggered by means of the function switching button 210 and the metering head 130 is set back into the holder 140 of the scale 110, and weighing takes place again (FIG. 13*c*).

Thereupon the glass punch 44 of the metering tool 40 is pulled slightly out of the glass tubule 42 of the tool, so that a holding chamber 43 is formed at the lower end of the metering tool 40 (FIG. 13*d*).

In the next step, the metering head 130 is manually guided above a storage container V containing substance to be taken up, and is immersed into this substance, thereby causing the holding chamber to be filled with the substance to be taken up (FIG. 13*e*).

Thereupon the metering head 130 is set back onto the scale 110, and checking takes place to determine whether the substance taken up is sufficient (FIG. 13*f*). In the case of an overly great amount (more metered in than was supposed to be), part of it is ejected back into the storage container V and weighing takes place again.

Subsequently, the metering head 130 is manually positioned above the substance receptacle (target container) A, and the substance amount situated in the holding chamber 43 of the metering tool 40 is ejected into the substance receptacle A. In this regard, the substance receptacle A is situated on a further scale 50, with which the amount of substance metered in can be measured in highly precise manner (FIG. 13*g*).

Thereupon the metering head 130 is weighed again (FIG. 13*h*), and finally, the metering tool 40 is ejected, unless it is supposed to be used again (FIG. 13*i*).

The metering process can also take place in multiple passes, using this metering head 130, as has already been described above.

By means of weighing the metering head 130 (with and without substance) in the different phases of the metering process, it can be determined very precisely how much substance was actually metered, and conclusions can also be drawn with regard to the excess of substance to be taken up, which amount can be different depending on the type of substance and the metering tools used. Thus, the metering tool can be calibrated to a certain extent, thereby making it possible to facilitate or optimize the work flow for further metering procedures with the respective substance. This holds true analogously also for the exemplary embodiment of FIGS. 1-8 and for the further exemplary embodiment described below.

In the following, a further embodiment of the metering apparatus according to the invention will be explained using FIGS. 14a-e. In this embodiment, the metering head, indicated as a whole as 230, is once again provided to be attached to the first scale 10 (FIG. 1), but is otherwise configured extensively similar to the metering head 130 of the embodiment according to FIGS. 11a and 12a-c. The following description is therefore essentially restricted to the particularities of the metering head 230 itself, and to a method sequence using this metering head, given as an example.

The metering head 230 comprises a tubular outer housing 230a and an inner housing 230b that is axially adjustable within the former. The outer housing 230a has a connection piece 211 that serves for mechanical attachment to the balance beam 11 on the first scale 10 (FIG. 1). The connection piece 211 can also have electrical contacts (not shown) for connecting the metering head with an external controller. A first raising and lowering device 232, which comprises a spindle 233 and a spindle motor 233a connected with the inner housing 230b, is disposed in the outer housing 230a. A groove 233b in the form of a helical line is provided on the spindle 233. The inner housing 230b can be axially raised and lowered in the outer housing 230a by means of the spindle motor 233a, wherein the spindle motor 233a also acts as a rotation mechanism whereby the inner housing 230b is simultaneously rotated about its axis R in the one direction or the other (arrows R' and R").

As in the exemplary embodiment of FIGS. 11a and 12a-c, a first and a second gripping tool 236 and 238 as well as a second raising and lowering device 234 are disposed in the inner housing 230b, wherein the second gripping tool 238 can be raised and lowered relatively to the locally fixed first gripping tool 236 by means of the second raising and lowering device 234. A conically configured guide opening 239 is provided at the lower end of the inner housing 230b, through which a metering tool 40 can be inserted into the metering head 230. More details in this regard are explained below.

The two gripping tools 236 and 238 and the first and second raising and lowering device 232 and 234 are fundamentally the same, in terms of design and function, as the corresponding components of the first exemplary embodiment of the metering apparatus, and therefore require no further explanation. The two gripping tools 236 and 238 and the two raising and lowering devices 232 and 234 are controlled by the external controller 100 (FIG. 1), as in the case of the first exemplary embodiment, wherein the metering head 230 is connected with the controller 100 by way of electrical contacts or in wireless manner. Of course, the metering head 230 can also be equipped with an internal controller 200, which can have functions analogous to those of the metering head 130.

Figures 14A, 14B, 14C:
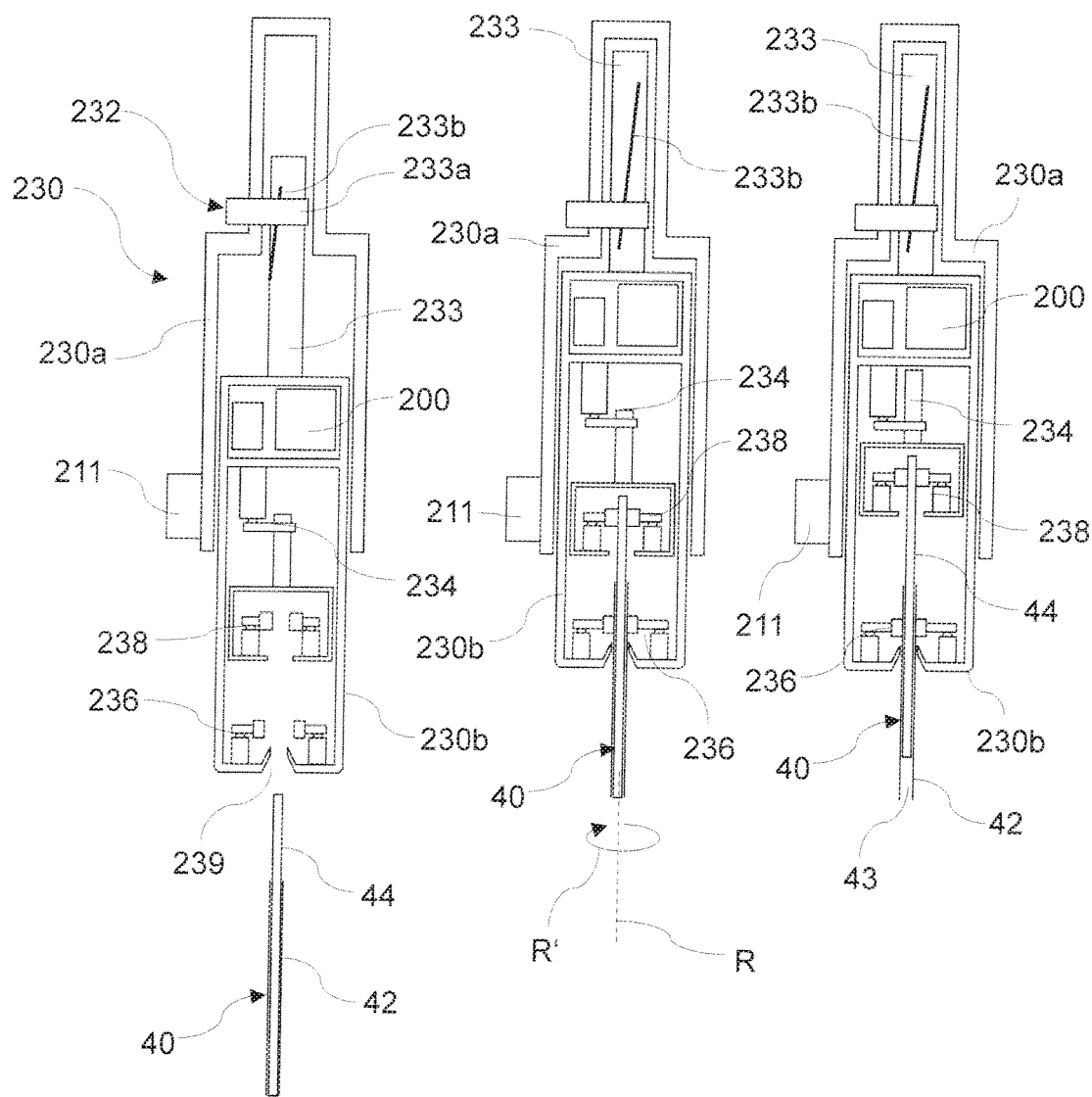

FIG. 14a shows the metering head 230 in a starting position, without the metering tool 40 being inserted as yet.

In FIG. 14b, the metering tool 40 is inserted, wherein the first and the second gripping tool 236 and 238 hold the glass tubule 42 and the glass punch 44 of the metering tool 40 in place, and the inner housing 230b is retracted upward into the outer housing 230a of the metering head 230. During the retraction movement, the inner housing 230b, and with it the metering tool 40 inserted into it, turns slightly about its longitudinal axis R, in the direction of the arrow R'.

In FIG. 14c the glass punch 44 of the metering tool 40 is pulled slightly out of the glass tubule 42, so that a metering chamber 43 is formed.

Figures 14D, 14E:
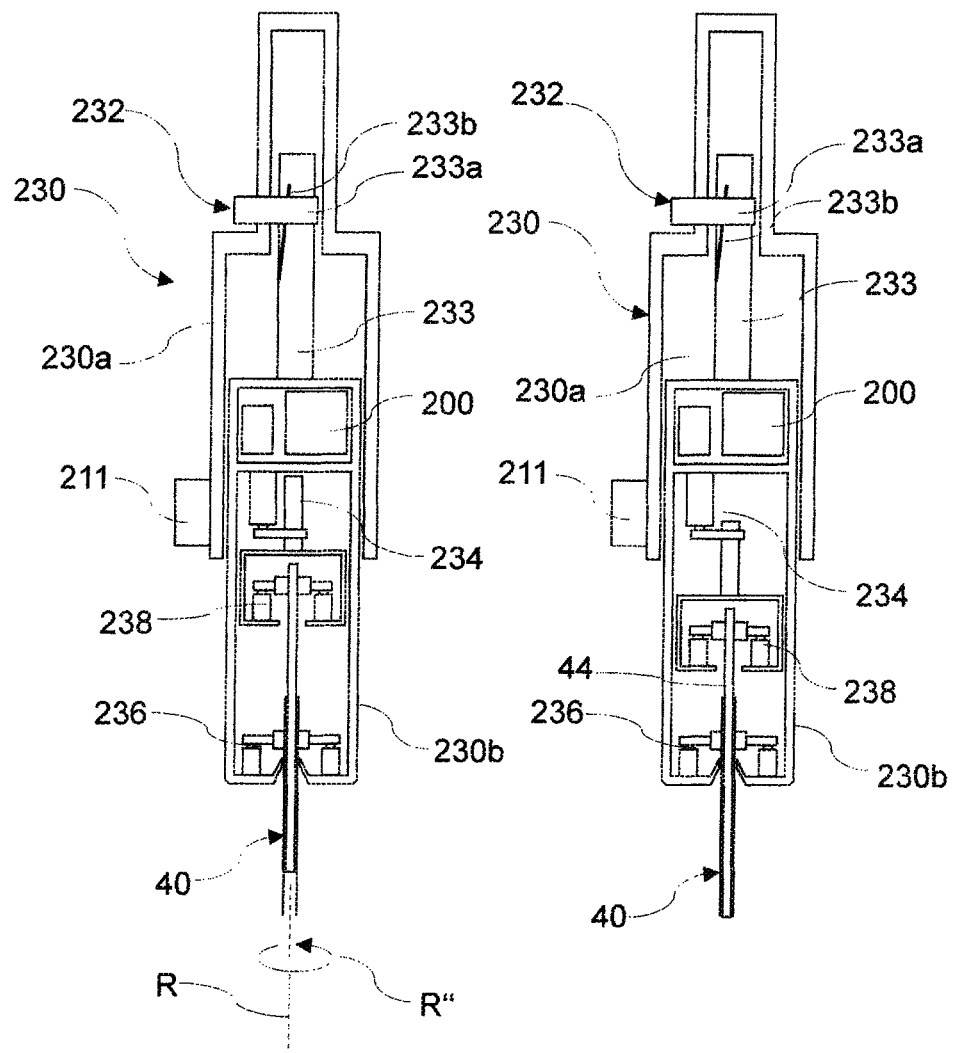

In this configuration, the metering head 230 is positioned above a storage vessel (not shown) during practical use, and the inner housing 230b is lowered, so that the metering tool 40 is immersed into the substance contained in the storage vessel or pierces it, so that a specific amount of the substance is taken up by the metering tool. During the lowering movement of the inner housing 230b, this housing, and with it the metering tool 40, rotates about its longitudinal axis R in the direction of the arrow R". The rotational movement of the metering tool 40 facilitates insertion in the case of substances having a relatively solid consistency. The rotational movement furthermore prevents sticking of the metering tool in the substance, and allows a substance plug to be drilled out in the case of certain substances. FIG. 14d shows the metering head 230 with the inner housing 230b lowered. Subsequently, the substance amount taken up by the metering tool 40 is ejected from the metering tool 40, in whole or in part, by lowering the glass punch 44 (FIG. 14e). The rotational movement of the metering tool 40 can furthermore also be implemented analogously in the exemplary embodiment according to FIGS. 1-8.

During practical use of the metering head 230, the individual steps of the metering method are the same as in the exemplary embodiment of the metering apparatus described using FIGS. 1-8, with the sole difference that in this metering head, the metering tool 40 additionally rotates slightly about its axis when it is lowered. Therefore no further explanation is required.

In some cases, the substance to be metered is present in the storage container V in crystallized form, as illustrated in FIGS. 15a-b. In this regard, the substance S often forms a crust on the bottom and on the side walls of the storage container. Even such a crystallized or crusty substance S can be scratched off and taken up by the metering apparatus according to the invention, i.e. its metering tool 40. In this regard, it is advantageous if the wall thickness of the glass tubule 42 of the metering tool 40 is relatively slight, preferably about in the range of 0.03 mm to 0.2 mm, preferably 0.03 mm to 0.1 mm. To take up the substance S, the storage container V is preferably held at a slant, so that the metering tool 40 slides along the side wall of the storage container V as the metering head is lowered and scrapes the substance off. This procedure can also be repeated multiple times until a sufficient substance amount has been taken up into the metering chamber or collects in an edge region of the storage container V, which substance can then be taken up from there.

The metering apparatus according to the invention makes it possible, using a single type of metering tool, to achieve precise 1:1 metering of the most varied substances, from powder, liquid, oily, sticky, viscous, wax-like to chocolate-like, apple-like, crystallized, crusty, etc. The cumbersome replacement of metering tools required for many metering apparatuses, depending on the consistency of the substance to be metered, is therefore completely eliminated. The metering apparatus according to the invention is suitable for practically all common storage containers and practically all common substance receptacles, without any kind of adapters. Using the metering apparatus according to the invention, highly precise metering can be carried out in a broad range, for example from several hundred mg to down into the sub-milligram range. The precision achieved is on the order of 0.01 mg and, in most cases, is better than with manual metering. The metering apparatus can work in full automation, depending on the embodiment, and is significantly faster than the manual metering still used in many cases.

The invention claimed is:

1. An apparatus for metering a substance,
having a metering head,
having a metering tool releasably attached to the metering head for taking up and dispensing a substance,
wherein the metering tool is configured as a cylindrical tubule having a punch slidably disposed therein, and forming a seal therewith, wherein the cylindrical tubule has a free edge at a lower end thereof adapted to be inserted within the substance, wherein the punch is longer than the tubule and projects out of the tubule at an upper end thereof and wherein the punch is slidable to project out of the tubule at both of the tubule ends simultaneously,
wherein the metering head is provided with a first gripping tool adapted to open and close for releasable clamping of the tubule and with a second gripping tool adapted to open and close for releasable clamping of the punch,
wherein the metering head is provided with a first raising and lowering device for raising and lowering the second gripping tool relative to the first gripping tool, thereby raising and lowering the punch in the tubule, and
wherein the apparatus comprises a rotation mechanism for rotating the metering tool about its longitudinal axis.

2. The apparatus according to claim 1, wherein the tubule or the punch is made of glass.

3. The apparatus according to claim 1, wherein the metering head has an internal controller for the first raising and lowering device and the first and the second gripping tools, as well as a function switching button that works together with the internal controller.

4. The apparatus according to claim 3, wherein the internal controller has an interface for communication with an external controller and/or for an external charging current source.

5. The apparatus according to claim 1, further comprising a first scale for the metering head and wherein the first scale is provided with a holder for the metering head.

6. The apparatus according to claim 5, wherein the holder is equipped with electrical contacts, which are configured for working together with corresponding electrical contacts on the metering head.

7. The apparatus according to claim 1, further comprising a first scale for the metering head and wherein the metering head is disposed on the first scale such that the first scale measures the weight of the metering head including any substance that has been taken up.

8. The apparatus according to claim 7, wherein the first scale is attached to a robot arm and the metering head is adjustable by the robot arm.

9. The apparatus according to claim 7, wherein the metering head comprises a second raising and lowering device for raising and lowering the first gripping tool together with the first raising and lowering device.

10. The apparatus according to claim 9, further comprising control electronics for the first scale and the raising and lowering device, as well as the first and the second gripping tool.

11. The apparatus according to claim 9, wherein the rotation mechanism is configured for rotating the metering tool about its longitudinal axis while it is being raised and lowered by the second raising and lowering device.

12. The apparatus according to claim 1, further comprising a second scale for weighing a substance receptacle.

13. The apparatus according to claim 1, wherein the tubule has an inside diameter between 0.1 and 5 mm.

14. The apparatus according to claim 1, wherein the tubule has a wall thickness between 0.03 and 0.2 mm.

15. The apparatus according to claim 1, wherein the tubule comprises a sharp edge at one end thereof.

16. The apparatus according to claim 1, further comprising a rack for a number of at least partially different metering tools.

17. The apparatus according to claim 1, wherein the tubule has an inside diameter between 0.1 and 1 mm.

18. The apparatus according to claim 1, wherein the tubule has a wall thickness between 0.03 and 0.1 mm.

19. A method for metering a substance, using an apparatus according to claim 1, comprising the following steps:
clamping the metering tool into the metering head by opening and closing the gripping tools,
positioning the metering tool above a substance storage container,
lowering the metering tool to insert the metering tool into a substance situated in the substance storage container, thereby taking substance up into a substance chamber of the metering tool,
raising the metering tool,
if applicable, lowering the punch of the metering tool relative to the tubule to eject excess substance,
positioning the metering tool above a substance receptacle, and
lowering the punch of the metering tool relative to the tubule to completely eject substance out of the metering tool into the substance receptacle.

20. The method according to claim 19, wherein the metering is carried out in individual partial metering steps, and during this process, monitoring by a scale, step-by-step approximation to a required target metering amount.

21. The method according to claim 19, wherein the amount of substance taken up by the metering tool is trimmed with monitoring by a scale.

22. The method according to claim 19, wherein the actual amount of the substance metered into the substance receptacle is measured by a scale.

23. The method according to claim 19, wherein the metering tool is rotated about its longitudinal axis while it is inserted into a substance contained in the substance storage container, and/or while it is pulled out of the substance.

24. The method according to claim 19, wherein a number of at least partially different metering tools is made available in a rack, and wherein the metering tool to be clamped is selected from among these metering tools that have been made available.

25. The apparatus according to claim 1, wherein the tubule has an inside diameter between 0.1 and 2 mm.

* * * * *